US005120712A

United States Patent [19]

Habener

[11] Patent Number: 5,120,712

[45] Date of Patent: Jun. 9, 1992

[54] INSULINOTROPIC HORMONE

[75] Inventor: Joel Habener, Newton Highlands, Mass.

[73] Assignee: The General Hospital Corporation, Boston, Mass.

[21] Appl. No.: 532,113

[22] Filed: Jun. 1, 1990

Related U.S. Application Data

[63] Continuation of Ser. No. 303,982, Jan. 30, 1989, abandoned, which is a continuation of Ser. No. 859,928, May 5, 1986, abandoned.

[51] Int. Cl.[5] .................... A61K 37/24; A61K 37/28; C07K 7/10; C07K 7/34

[52] U.S. Cl. .................................... 514/12; 514/866; 530/324; 530/303; 530/308

[58] Field of Search ...................... 530/324, 303, 308; 514/12, 866

[56] References Cited

FOREIGN PATENT DOCUMENTS 0044168 1/1982 European Pat. Off. .
0082731 12/1982 European Pat. Off. .

OTHER PUBLICATIONS

Mojsov et al., *J. Clin. Invest.*, vol. 79, pp. 616-619 (Feb. 1987).
Blackmore et al., *FEBS Lett.*, 283:7-10 (1991).
Weir, G. C. et al., *Diabetes*, 38(3):338-342 (Mar. 1989).
Gefel, D. et al., *Endocrinology*, 126(4):2164-2168 (1990).
Patzelt et al., *Nature*, 282:260-266 (1979).
Shields et al., *Nature*, 289:511-514 (1981).
Lund et al., *Proc. Natl. Acad. Sci. (USA)*, 79:345-9 (1982).
Bell et al., *Nature*, 302:716-718 (1983).
Lopez et al., *Proc. Natl. Acad. Sci. (USA)*, 80:5485-5489 (1983).
Andrews et al., *J. Biol. Chem.*, 260:3910-3914 (1985).
Heinrich et al., *Endocrinol.*, 115:2176-2181 (1984).
Ghiglione et al., *Diabetologia*, 27:599-600 (1984).
Uttenthal et al., *J. Clin. End. Metab.*, 61:472-479 (1985).
Moody et al., *Nature*, 289:514-516 (1981).
Yanaihara et al., *FEBS Letters*, 187:307-310 (1985).
Hoosein et al., *FEBS Letters*, 178:83-86 (1984).
Korman et al., *Diabetes*, 34:717-722 (1985).
Ghiglione et al., *Regulatory Peptides*, 13:101, Abs. (1985).
Schmidt et al., *Diabetologia* et al., 28:704-707 (1985).
Holst et al., *FEBS*, vol. 211, No. 2, pp. 169-174 (Jan. 26, 1987).
Orskov et al., *Endocrinology*, vol. 119, No. 4, pp. 1467-1475 (Oct. 1986).
Rudinger, *Peptide Hormones. Parsons* (ed.), U. Parle Press, Baltimore, pp. 1-7 (1976). .
Ganong, W., *Review of Medical Physiology*, 9th Ed., Lange Medical Publications, Los Altos, Calif., (1976), pp. 257-276.
Drucker, D., et al., *Proc. Natl. Acad. Sci. (USA)*, 84:3434-3438 (May 1987).

*Primary Examiner*—Lester L. Lee
*Assistant Examiner*—Christina Chan
*Attorney, Agent, or Firm*—Sterne, Kessler, Goldstein and Fox

[57] ABSTRACT

A fragment of glucagon-like peptide I (GLP-1) has been found to be an insulinotropic hormone. This insulinotropic hormone comprises amino acid residues 7-37 of GLP-1. The insulinotropic hormone is useful as a potential therapy for *Diabetes Mellitus*.

10 Claims, 7 Drawing Sheets

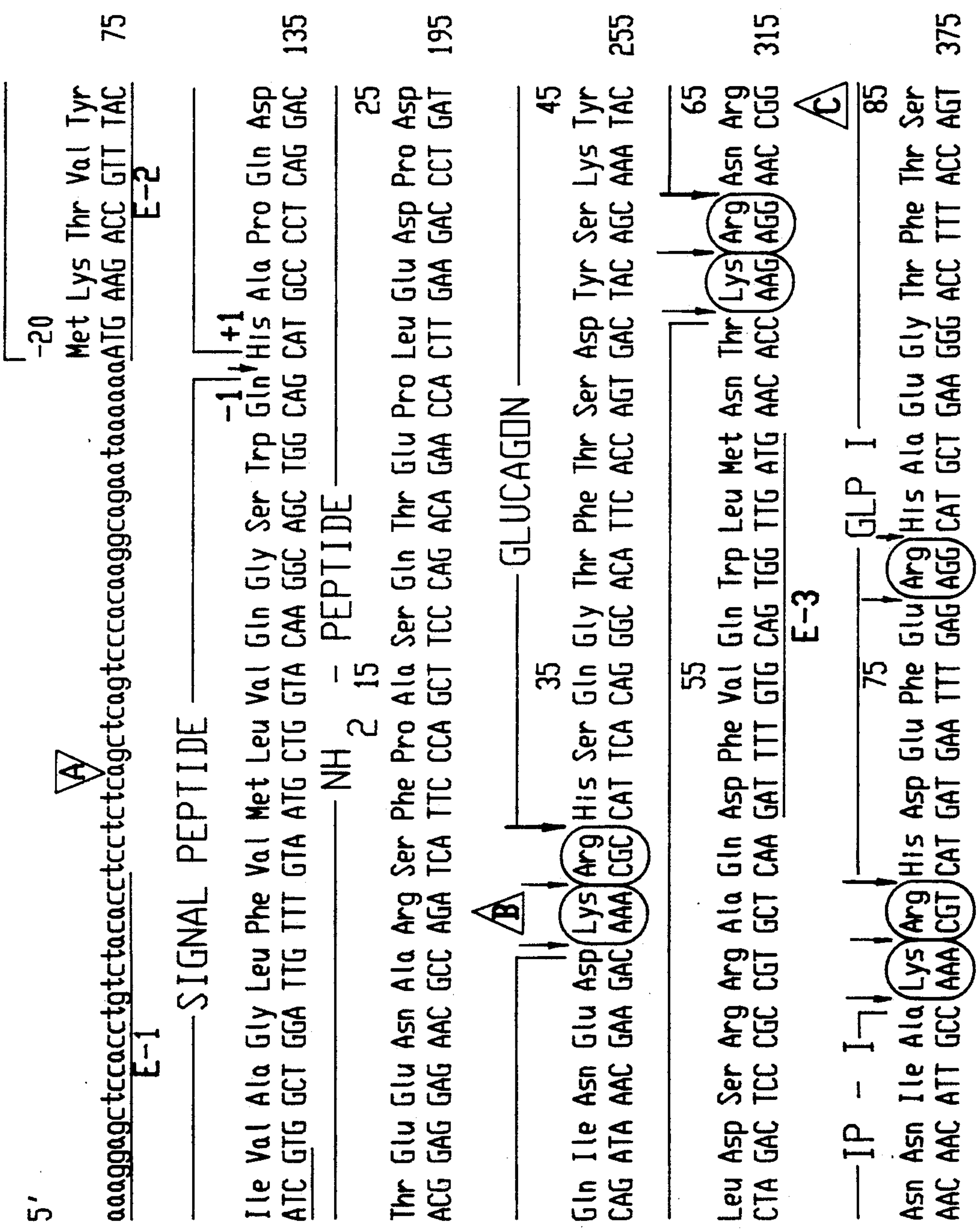

FIG.1A

5'
aaggggctccacctgtctacacctccttctcagctcagtcccacaaggcagaataaaaaaATG AAG ACC GTT TAC
　　　　　　　　　　　　　　　　　　　　　　　　　　　　　　　　　　Met Lys Thr Val Tyr
　　　　　　　　　　　　　　　△A　　　　　　　　　　　　　　　　　　　−20
　　　E-1　　　　　　　　　　　　　　　　　　　　　　　　　　　　　　　　　　　　　E-2　　75

———SIGNAL PEPTIDE———                            −1 ↓ +1
Ile Val Ala Gly Leu Phe Val Met Leu Val Gln Gly Ser Trp Gln His Ala Pro Gln Asp
ATC GTG GCT GGA TTG TTT GTA ATG CTG GTA CAA GGC AGC TGG CAG CAT GCC CCT CAG GAC
                                                                              135
                                  ———NH₂ - PEPTIDE———                          25
Thr Glu Glu Asn Ala Arg Ser Phe Pro Ala Ser Gln Thr Glu Pro Leu Glu Asp Pro Asp
ACG GAG GAG AAC GCC AGA TCA TTC CCA GCT AGT CAG ACA GAA CCA CTT GAA GAC CCT GAT
　　　　　　　　　　　　　　　　△B
　　　　　　　　　　　　　　　　　　　　　　　　　　　　　　　　　　　　　　　195
　　　　　　　　　　　　　　　　　　　　　　　　　　　———GLUCAGON———
　　　　　　　　　　　　　　　　　　　　　　　　　　　　35　　　　　　　　　　　　45
Gln Ile Asn Glu Asp Lys Arg His Ser Gln Gly Thr Phe Thr Ser Asp Tyr Ser Lys Tyr
CAG ATA AAC GAA GAC AAA CGC CAT TCA CAG GGC ACA TTC ACC AGT GAC TAC AGC AAA TAC
　　　　　　　　　　　　　　　　　　　　　　　　　　　　　　　　　　　　　　255
　　　　　　　　　　　　　　　　　　　　　　　　　　　　　　　　　　　　　　　65
Leu Asp Ser Arg Arg Ala Gln Asp Phe Val Gln Trp Leu Met Asn Thr Lys Arg Asn Arg
CTA GAC TCC CGC CGT GCT CAA GAT TTT GTG CAG TGG TTG ATG AAC ACC AAG AGG AAC CGG
　　　　　　　　　　　　　　　　　　　　　　　　　　　　　　　　　　　　　　315
　　　　　　　　　　　　　　　　　　　　　　　　　　　　　△C
　　　　E-3　　　　　　　　　　　　　　　　　———GLP I———
———IP - I———　　　　　　75　　　　　　　　　　　　　　　　　　　　85
Asn Asn Ile Ala Lys Arg His Asp Glu Phe Glu Arg His Ala Glu Gly Thr Phe Thr Ser
AAC AAC ATT GCC AAA AGG CAT GAT GAA TTT GAG AGG CAT GCT GAA GGG ACC TTT ACC AGT
                                                                              375

```
                                                          105  (NH₂)
Asp Val Ser Ser Tyr Leu Glu Gly Gln Ala Ala Lys Glu Phe Ile Ala Trp Leu Val Lys    435
GAT GTG AGT TCT TAC TTG GAG GGC CAG GCA GCA AAG GAA TTC ATT GCT TGG CTG GTG AAA
                         95                        ─────────── E-4 ───────────

                                                   ↓ 125
         (NH₂)            ────── IP-II ──────    NH₂
Gly Arg┆Gly┆Arg┆Arg┆Asp Phe Pro Glu Val Ala Ile Ala Glu Glu Leu┆Gly┆Arg┆Arg┆       495
GGC CGA│GGA│AGG│CGA│GAC TTC CCG GAA GTC GCC ATA GCT GAG GAA CTT│GGG│CGC│AGA│
                  Ⓐ                    115                              
                                 ─────────── GLP ───────────                     
                                                                                 145
His Ala Asp Gly Ser Phe Ser Asp Glu Met Asn Thr Ile Leu Asp Asn Leu Ala Thr Arg   555
CAT GCT GAT GGA TCC TTC TCT GAT GAG ATG AAC ACG ATT CTC GAT AAC CTT GCC ACC AGA
              ─────────── E-5 ───────────
                                     135
                                                           ↓
Asp Phe Ile Asn Trp Leu Ile Gln Thr Lys Ile Thr Asp┆Lys┆Lys┆End
GAC TTC ATC AAC TGG CTG ATT CAA ACC AAG ATC ACT GAC│AAG│AAA│TAG gaatatttccaccatt  618
                               155                   Ⓔ

cacaaccatctttcacaacatcttcctgccagtcacttgggatgtacatttgagagcatatccgaagctatactgctttgc  697
─────────── E-6 ───────────
atgcggacgaatacatttccctttagcgttgtgtaaccaaaggttgtaaatggaataagttttttccagggtgttgat    776
aaagtaacaacttacagtatgaaaatgctggattctcaaatgtctcctcgttttgaagttaccgcccctgagattact    855
ttcctggtataattatcgcagtcacgacacctggattacaacacagaagacatggtaacctggtaacc              933
gtagtggtgaacctgaaagagaacttcttcctgaaccccttgtcataaatgcgctcagcttttcaatgtatcaagaat   1012
agatttaaataaatatctcat  3'                                                       1024
```

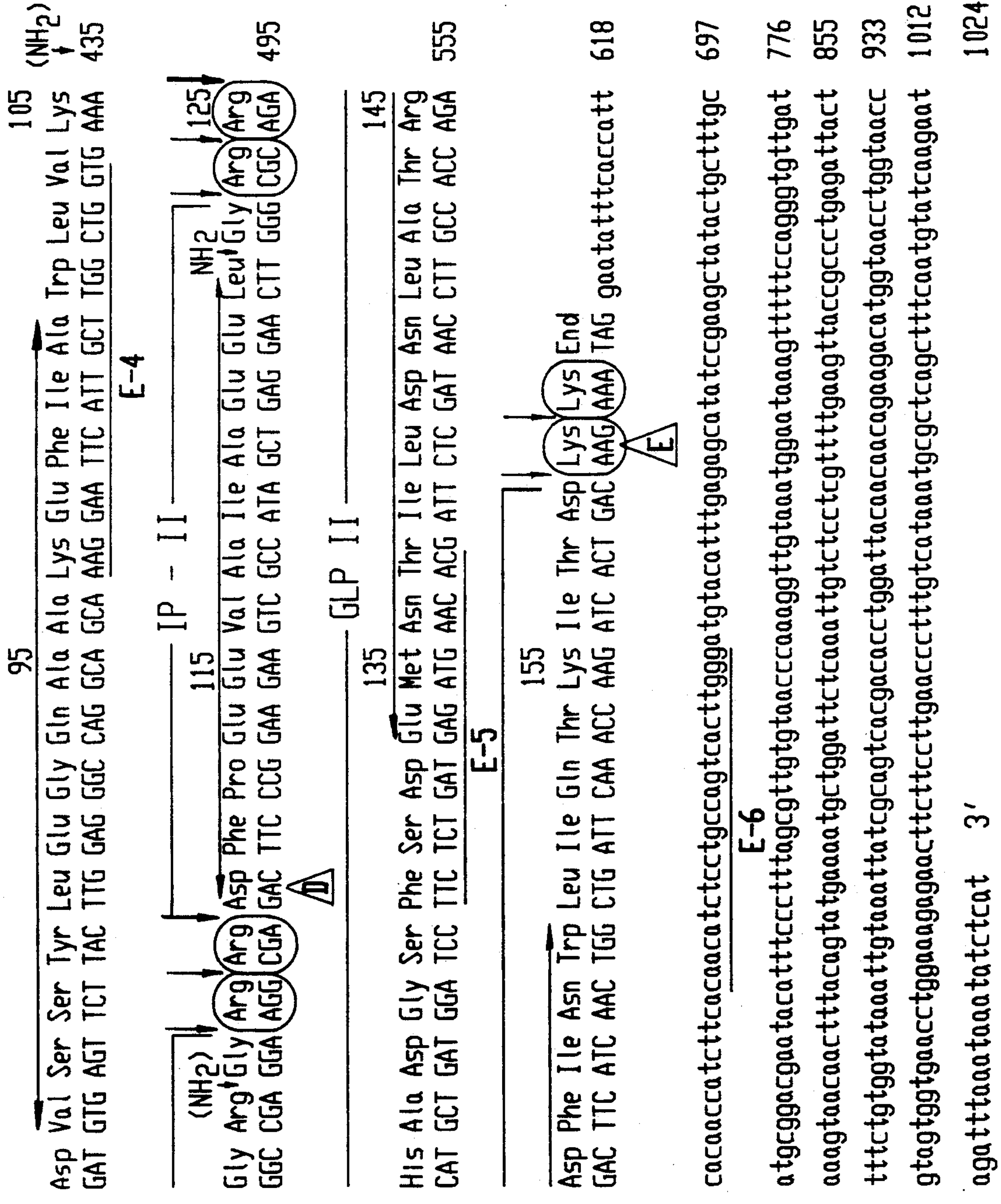

FIG. 1B

INSULINOTROPIC HORMONE

This application is a continuation of application Ser. No. 07/303,982, filed Jan. 30, 1989, now abandoned, which is a continuation of U.S. patent application Ser. No. 06/859,928, filed on May 5, 1986, and now abandoned.

BACKGROUND OF THE INVENTION

1. Field of the Invention

This invention is directed to the discovery that certain peptide fragments of the prehormone, proglucagon, possess hormonal activities and can be used to stimulate the synthesis and secretion of the hormone, insulin. These peptide fragments are useful in therapy for the disease *Diabetes mellitus.*

2. Description of the Background Art

The endocrine secretions of the pancreatic islets are under complex control not only by blood-borne metabolites (glucose, amino acids, catecholemines, etc.), but also by local paracrine influences. The major pancreatic islet hormones (glucagon, insulin and somatostatin) interact amongst their specific cell types (A, B, and D cells, respectively) to modulate secretory responses mediated by the metabolites. Although insulin secretion is predominantly controlled by blood levels of glucose, glucagon and somatostatin stimulate and inhibit glucose-mediated insulin secretory responses, respectively. In addition to the proposed interislet paracrine regulation of insulin secretion, there is evidence to support the existence of insulinotropic factors in the intestine. This concept originates from the observations that glucose taken orally is a much more potent stimulant of insulin secretion than is a comparable amount of glucose given intravenously.

The human hormone, glucagon, is a 29-amino acid peptide hormone produced in the A-cells of the pancreas. The hormone belongs to a multi-gene family of structurally related peptides that include secretin, gastric inhibitory peptide, vasoactive intestinal peptide and glicentin. These peptides variously regulate carbohydrate metabolism, gastrointestinal mobility and secretory processing. The principal recognized actions of pancreatic glucagon, however, are to promote glycogenolysis and gluconeogenesis, resulting in an elevation of blood sugar levels. In this regard, the actions of glucagon are counterregulatory to those of insulin and may contribute to the hyperglycemia that accompanies *Diabetes mellitus* (Lund, P. K. et al., *Proc. Natl. Acad. Sci., U.S.A.,* 79: 345-349 (1982)

Glucagon has been found to be capable of binding to specific receptors which lie on the surface of insulin producing cells. Glucagon, when bound to these receptors, stimulates the rapid synthesis of cAMP, by these cells. cAMP, in turn, has been found to stimulate insulin expression (Korman, L. Y. et al., *Diabetes,* 34:717-722 (1985)). Insulin acts to inhibit glucagon synthesis (*Review of Medical Physiology,* Ganong, W. F., 1979 Lange Publications, Los Altos, California (p. 273). Thus the expression of glucagon is carefully regulated by insulin, and ultimately by the serum glucose level.

The glucagon gene is initially translated from a 630 base pair precursor to form the polypeptide, preproglucagon (Lund et al. *Proc. Natl. Acad. Sci. U.S.A.* 79:345-349 (1982)). This polypeptide is subsequently processed to form proglucagon. Patzelt, C. et al., *Nature,* 282: 260-266 (1979), demonstrated that proglucagon was subsequently cleaved into glucagon and a second polypeptide. Subsequent work by Lund, P. K. et al., Lopez L. C. et al., (*Proc. Natl. Acad. Sci. U.S.A.* 80:5485-5489 (1983)) and Bell, G. I. et al., (*Nature*) 302:716-718 (1983) demonstrated that the proglucagon molecule was cleaved immediately after lysine-arginine dipeptide residues. Studies of proglucagon produced by channel catfish (*Ictalurus punctata*) indicated that glucagon from this animal was also poteolytically cleaved after adjacent lysine-arginine and arginine-arginine dipeptide residues (Andrews P. C. et al., *J. Biol. Chem.,* 260: 3910-3914 (1985)). Lopez, L. C. et al., (*Proc. Natl. Acad. Sci. U.S.A.* 80:5485-5489 (1983)), and Bell, G. I. et al, discovered the mammalian proglucagon was cleaved at lysine-arginine or arginine dipeptides, and demonstrated that the proglucagon molecule contained three discreet and highly homologous peptide molecules which were designated glucagon, glucagon-like protein 1 (GLP-1) and glucagon-like protein 2 (GLP-2). Lopez et al. concluded that glucagon-like protein 1 was 37 amino acid residues long and that glucagon-like peptide 2 was 34 amino acid residues long. Analogous studies on the structure of rat preproglucagon revealed a similar pattern of proteolytic cleavage between adjacent lysine-arginine or arginine-arginine dipeptide residues, resulting in the formation of glucagon, GLP-1 and GLP-2 (Heinrich, G. et al., *Endocrinol.,* 115: 2176-2181 (1984)). Human rat, bovine, and hamster sequences of GLP-1 have been found to be identical (Ghiglione, M. et al., *Diabetologia,* 27:599-600 (1984)).

The conclusion reached by Lopez et al. regarding the size of GLP-1 was confirmed by the work of Uttenthal, L. O. et al. (*J. Clin. Endocrinol. Metabol.,* 61: 472-479 (1985)). Uttenthal et al. examined the molecular forms of GLP-1 which were present in the human pancreas. Their research shows that GLP-1 and GLP-2 are present in the pancreas as 37 amino acid and 34 amino acid peptides, respectively.

The similarity between GLP-1 and glucagon suggested to early investigators that GLP-1 might have biological activity. Although some investigators found that GLP-1 could induce rat brain cells to synthesize cAMP (Hoosein, N. M. et al., *Febs Lett.* 178:83-86 (1984)), other investigators failed to identify any physiological role for GLP-1 (Lopez, L. C. et al.). The failure to identify any physiological role for GLP-1 caused some investigators to question whether GLP-1 was in fact a hormone and whether the relatedness between glucagon and GLP-1 might be artifactual (Ghiglione, M. et al.).

Thus, in conclusion, the prior art reveals an awareness of the processing of a glucagon hormone precursor into a set of peptides sharing extensive homology. It has been widely assumed by those of skill in the art that these highly related glucagon-like peptides would have a biological activity. Nevertheless, extensive investigations designed to elucidate the biological effects of these molecules had been unsuccessful.

SUMMARY OF THE INVENTION

The hormone glucagon is known to be synthesized as a high molecular weight precursor molecule which is subsequently proteolytically cleaved into three peptides: glucagon, glucagon-like peptide 1 (GLP-1) and glucagon-like peptide 2 (GLP-2). GLP-1 has 37 amino acids in its unprocessed form. This invention discloses that the unprocessed GLP-1 is naturally converted to a 31 amino acid long peptide (7-37 peptide) having amino acids 7-37 of GLP-1. This processing occurs in the pancreas and the intestine. The 7-37 peptide is an insulinotropic hormone which had not previously been described. The hormone's activity appears to be specific for the pancreatic beta, cells where it appears to induce the biosynthesis of insulin. The unprocessed GLP-1 peptide is essentially unable to mediate the induction of insulin biosynthesis. The insulinotropic hormone is useful in the study of the pathogenesis of maturity onset diabetes mellitus, a condition in which the dynamics of insulin secretion are abnormal. Moreover, the insulinotropic hormone is useful in therapy for this disease.

BRIEF DESCRIPTION OF THE DRAWINGS

FIG. 1 shows the DNA structure and corresponding amino acid sequence of human, rat and hamster preproglucagons. The preproglucagon precursor is proteolytically cleaved at sites indicated by circles.

DESCRIPTION OF THE PREFERRED EMBODIMENTS

Figure 2:
FIG. 2 shows the effect of GLP-1 peptides on insulin mRNA levels in rat insulinoma cells.

Peptide moieties (fragments) chosen from the determined amino acid sequence of human GLP-1 constitute the starting point in the development comprising the present invention. The amino acid sequence for GLP-1 has been reported by several researchers (Lopez, L. C., et al., *Proc. Natl. Acad. Sci. U.S.A.* 80:5485-5489 (1983); Bell, G. R., et al., *Nature* 302:716-718 (1983); Heinrich, G., et al., *Endocrinol.* 115:2176-2181 (1984); Ghiglione, M., *Diabetologia* 27:599-600 (1984)). The structure of the preproglucagon gene and its corresponding amino acid sequence is shown in FIG. 1. This figure further displays the proteolytic processing of the precursor gene product into glucagon and the two glucagon-like peptides. As used herein, the notation GLP-1 (1-37) refers to a GLP-1 polypeptide having all amino acids from 1 (N-terminus) through 37 (C-terminus). Similarly, GLP-1 (7-37) refers to a GLP-1 polypeptide having all amino acids from 7 (N-terminus) through 37 (C-terminus).

In one embodiment, the peptide fragments are synthesized by the well-known solid phase peptide synthesis described by Merrifield, J. M., *Chem. Soc.* 85: 2149 (1962), and Stewart and Young, *Solid Phase Peptide Synthesis* (Freeman, San Francisco, 1969), pages 27-66, which are incorporated by reference herein. However, it is also possible to obtain fragments of the proglucagon polypeptide or of GLP-1 by fragmenting the naturally-occurring amino acid sequence, using, for example, a proteolytic enzyme. Further, it is possible to obtain the desired fragments of the proglucagon peptide or of GLP-1 through the use of recombinant DNA technology, as disclosed by Maniatis, T. et al., *Molecular Biology: A Laboratory Manual,* Cold Spring Harbor, NY 1982, which is hereby incorporated by reference.

The invention pertains to a peptide fragment which is insulinotropic and is derivable from a naturally-occurring amino acid sequence.

The invention comprises a peptide fragment having the following amino acid sequence:

His—Ala—Glu—Gly—Thr—Phe—Thr—Ser—Asp—

Val—Ser—Ser—Tyr—Leu—Glu—Gly—Gln—Ala—

Ala—Lys—Glu—Phe—Ile—Ala—Trp—Leu—Val—

Lys—Gly—Arg—Gly— and functional derivatives thereof, these fragments and functional derivatives being substantially free of natural contaminants and having insulinotropic activity.

Of particular interest are peptides of the following formula:

$H_2N—X—CO—R^1$ wherein $R^1$ is OH OM or $—NR^2R^3$;

M is a pharmaceutically acceptable cation or a lower (Cl-C6) branched or unbranched alkyl group; R2 and R3 are the same or different and selected from the group consisting of hydrogen and a lower ($C_1$-$C_6$) branched or unbranched alkyl group; and $H_2N—X—CD$ is the amino acid sequence or peptide fragment described above, the "$H_2N$" being the amine group of the amino terminus of X and the "CO" being the carboxyl group of the carboxyl terminus of X;

(2) The acid addition salts thereof; and (3) The protected or partially protected derivatives thereof.

The invention further pertains to a method for enhancing the expression of insulin which comprises:

providing to a mammalian pancreatic B-type islet cell an effective amount of the insulinotropic peptides disclosed above.

Included within the scope of the present invention are those amino acid sequences in the above peptides which are capable of functioning as insulinotropic hormones. Included as well are the use of additional amino acid residues added to enhance coupling to carrier protein or amino acid residues added to enhance the insulinotropic effect. A material is said to be "substantially free of natural contaminants" if it has been substantially purified from materials with which it is normally and naturally found. Examples of natural contaminants with which GLP-1 (7-37) might be associated are: other peptides, carbohydrates, glycosylated peptides, lipids, membrane, etc. A material is also said to be substantially free of natural contaminants if these contaminants are substantially absent from a sample of the material.

The interchangeable terms "peptide fragment" and "peptide moiety" are meant to include both synthetic and naturally-occurring amino acid sequences derivable from a naturally occurring amino acid sequence.

A peptide is said to be "derivable from a naturally-occurring amino acid sequence" if it can be obtained by fragmenting a naturally-occurring sequence, or if it can be synthesized based upon a knowledge of the sequence of the naturally occurring amino acid sequence or of the genetic material (DNA or RNA) which encodes this sequence.

The invention further pertains to polypeptides that, in addition to the chosen sequence, may contain or lack one or more amino acids that may not be present in the naturally-occurring sequence wherein such polypeptides are functionally similar to the chosen polypeptide. Such polypeptides for the present invention, are termed "functional derivatives," provided that they demonstrate insulinotropic activity which is substantially similar to that of GLP-1 (7–37).

An "insulinotropic activity" relates to the ability of a substance to stimulate, or cause the stimulation of, the synthesis or expression of the hormone insulin.

As is known in the art, the amino acid residues may be in their protected or unprotected form, using appropriate amino or carboxyl protecting groups. Useful cations are alkali or alkaline earth metallic cations (i.e., Na, K, Li, ½ Ca, ½ Ba, etc.) or amine cations (i.e., tetraalkylammonium, trialkylammonium, where alkyl can be $C_1$–$C_{12}$).

The variable length peptides may be in the form of the free amines (on the N-terminus), or acid-addition salts thereof. Common acid addition salts are hydrohalic acid salts, i.e., HBr, HI, or more preferably, HCl.

The insulinotropic property of a compound may be determined by providing that compound to animal cells, or injecting that compound into animals and monitoring the release of immunoreactive insulin (IRI) into the media or circulatory system of the animal, respectively. The presence of IRI is detected through the use of a radioimmunoassay which can specifically detect insulin. Although any radioimmunoassay capable of detecting the presence of IRI may be employed, it is preferable to use a modification of the assay method of Albano, J. D. M., et al. (*Acta Endocrinol.* 70: 487–509 (1972)). In this modification a phosphate/albumin buffer with a pH of 7.4 was employed. The incubation was prepared with the consecutive condition of 500 ul of phosphate buffer, 50 ul of perfusate sample or rat insulin standard in perfusate, 100 ul of anti-insulin antiserum (Wellcome Laboratories; 1:40,000 dilution), and 100 ul of [$^{125}$I] insulin, giving a total volume of 750 ul in a 10×75-mm disposable glass tube. After incubation for 2–3 days at 4° C., free insulin was separated from antibody-bound insulin by charcoal separation. The assay sensitivity was 1–2 uU/ml. In order to measure the release of IRI into the cell culture medium of cells grown in tissue culture, one preferably incorporates radioactive label into proinsulin. Although any radioactive label capable of labelling a polypeptide can be used, it is preferable to use $^3$H leucine in order to obtain labelled proinsulin. Labelling can be done for any period of time sufficient to permit the formation of a detectably labelled pool of proinsulin molecules; however, it is preferable to incubate cells in the presence of radioactive label for a 60 minute time period. Although any cell line capable of expressing insulin can be used for determining whether a compound has an insulinotropic effect, it is preferable to use rat insulinoma cells, and especially RIN - 38 rat insulinoma cells. Such cells can be grown in any suitable medium; however, it is preferable to use DME medium containing 0.1% BSA and 25 mM glucose.

The insulinotropic property of a compound may also be determined by pancreatic infusion. The in situ isolated perfused rat pancreas preparation was a modification of the method of Penhos, J. C. et al., (*Diabetes,* 18:733–738 (1969)). Fasted male Charles River strain albino rats, weighing 350–600 g, were anesthetized with an intraperitoneal injection of Amytal Sodium (Eli Lilly and Co.; 160 ng/kg). Renal, adrenal, gastric, and lower colonic blood vessels are ligated. The entire intestine was resected except for about four cm of duodenum and the descending colon and rectum. Therefore, only a small part of the intestine was perfused, thus minimizing possible interference by enteric substances with glucagon-like immunoreactivity. The perfusate was a modified Krebs-Ringer bicarbonate buffer with 4% dextran T70 and 0.2% bovine serum albumin (fraction V), and was bubbled with 95% $O_2$ and 5% $CO_2$. A nonpulsatile flow, 4-channel roller bearing pump (Buchler polystatic, Buchler Instruments Division, Nuclear-Chicago Corp.) was used, and a switch from one perfusate source to another was accomplished by switching a 3-way stopcock. The manner in which perfusion was performed, monitored, and analyzed followed the method of Weir, G. C. et al. (*J. Clin. Investigat.* 54: 1403–1412 (1974)), which is hereby incorporated by reference.

The compounds of the present invention can be formulated according to known methods to prepare pharmaceutically useful compositions, whereby GLP-1 (7–37) or its functional derivatives are combined in admixture with a pharmaceutically acceptable carrier vehicle. Suitable vehicles and their formulation, inclusive of other human proteins, e.g. human serum albumin, are described for example in *Remington's Pharmaceutical Sciences* (16th Ed. A. Oslo Ed. Mack, Easton PA (1980)). In order to form a pharmaceutically acceptable composition suitable for effective administration, such compositions will contain an effective amount of the GLP-1 (7–37), or its functional derivatives, together with a suitable amount of carrier vehicle.

Compositions containing GLP-1 (7–37) or its functional derivatives may be administered intravenously, intramuscularly, or subcutaneously at dosages in the range of from about 1 pg/kg to 1,000 ug/kg body weight, although a lower or higher dosage may be administered. The required dosage will depend upon the severity of the condition of the patient and upon such criteria as the patient's height, weight, sex, age, and medical history.

For the purpose of parenteral administration, compositions containing GLP-1 (7–37) are dissolved in distilled water and the pH-value is adjusted to about 6 to 8. In order to facilitate the lyophilization process resulting in a suitable product, lactose could be added to the solution. The solution is then filter sterilized, introduced into vials, and lyophilized. The concentration of GLP-1 (7–37) in these compositions may vary from $10^{-12}$M to $10^{-5}$M.

Additional pharmaceutical methods may be employed to control the duration of action. Controlled release preparations may be achieved by the use of polymers to complex or adsorb GLP-1 (7–37) or its functional derivatives. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release. Another possible method to control the duration of action by controlled release preparations is to incorporate GLP-1 (7–37) into particles of a polymeric material such as polyesters, polyamino acids, hydrogels, poly (lactic acid) or ethylene vinylacetate copolymers. Alternatively, instead of incorporating GLP-1 (7–37) into these polymeric particles, it is possible to entrap GLP-1 (7–37) in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences* (1980).

SPECIFIC EXAMPLES

Example 1

Rat insulinoma cells of cell line RIN-38 were derived from a continuous islet cell line, RIN-r, which was established from a transplantable rat islet cell tumor (Gazdar, A. F. et al., *Proc. Nat'l Acad. Sci. U.S.A.* 77: 3519-3523 (1980)). The cells were maintained in DMEM (Gibco) at a glucose concentration of 4,500 mg/L, and supplemented with 10% heat-inactivated fetal bovine serum (Gibco), 100 U/ml of penicillin and 100 ug/ml of streptomycin. Incubations were carried out at 37° C. in 95% air: 5% $CO_2$. Cells grown in the above manner were washed and resuspended in DMEM (Gibco) containing 0.1% bovine serum albumin and 25 mM glucose. Cells were incubated with varying concentrations of GLP-1 (1-37), GLP-1 (7-37) or GLP-1 (1-36 des-gly-arg amide) for six hours, following which the effects of these agents on insulin mRNA expression were determined. Cellular RNA was analyzed for insulin specific mRNA as follows: cellular RNA was extracted from solid tumors and cells by homogenization in guanadine thiocyanate and sedimentation through a cesium chloride cushion. Poly A+RNA was isolated by oligo dT cellulose chromatography (Aviv, H. et al., *Proc. Natl Acad. Sci. U.S.A.* 69: 1408-1412 (1972)). 20 ug of total RNA from each sample was fractionated by size on a 1.4% agarose gel after denaturation in glyoxal, followed by electrotransfer to a nylon membrane (Nytran; Schleicher and Schuell). Blotted membranes were baked for two hours at 80° C. under vacuum, prehybridized in lM NaCl / 1% SDS/ 10% Dextran sulfate at 50° C. overnight and hybridized at the same temperature for 24 h after addition of the labelled probes (3-5×$10^5$ cpm/ml); they were then washed at 55° C. twice in 1×SSC (0.15 M NaCl / 0.015M Na citrate)/1% SDS), and exposed to X-ray film for varying times at −70° C. with an intensifying screen. In all cases the concentration of peptides was $10^{-7}$M.

The result of this experiment is shown in FIG. 2. Lanes 1-3(control cells), 4-6(GLP-1 (1-37)), 7-9 GLP-1 (7-37), 10-12 (GLP-1(1-36 des- gly arg -amide) shows the amount of insulin specific mRNA produced. Triplicate experimental results are presented for each peptide.

Using a microdensitometer the relative amounts of insulin specific mRNA were determined. This experiment revealed that, at equal peptide concentrations, GLP-1 (7-37) stimulated insulin gene expression to more than 3 times the level found in control (untreated) cells.

Example 2

Rat insulinoma cells of cell line RIN-38 were grown in DME medium as described in Example 1. After incubation with $10^{-7}$M GLP-1 (1-37, GLP-1 (7-37) and GLP-1 (1-36), the concentrations of insulin in the cell culture mediums were determined by radioimmunassay (as described above). Insulin protein levels were determined after incubation for six hours. The results of this experiment are shown in Table 1.

TABLE 1

| PEPTIDE ADDED | Insulin Produced (uUnits/ML) |
|---|---|
| None | 2800 |
| GIP-1 (1-37) | 5000 |

Example 3

The pancreas of live rat was perfused with varying concentrations of GLP-1 (1-37) and GLP-1 (7-37) as described above. At one minute intervals, rat serum insulin levels in picograms/ml were determined by radioimmunassay (as described above). The results of this experiment are shown in Table 2. Perfusions were done using peptide concentrations of 5×$10^{-7}$M, 5×$10^{-8}$M, 5×$10^{10}$M and 5×$10^{-11}$M and 5×$10^{12}$ M. Peptides were added after the zero minute serum value had been determined.

GLP-1 (1-37) was found to mediate a 3.4-fold increase in serum insulin concentrations when perfused into rat pancreas at a concentration of 5×$10^{-7}$M; at a concentration of 5×$10^{-8}$M this peptide was capable of mediating only a 2-fold increase in serum insulin levels. At a concentration of 5×$10^{-10}$M this peptide was found to mediate only a 20% increase in serum insulin levels.

GLP-1 (7-37) was found to be capable of stimulating a 132-fold increase in insulin levels when provided to rat pancreas at a concentration of 5×$10^{-7}$M. At a 10-fold lower concentration (5×$10^{-8}$M) this peptide was capable of directing a 21-fold increase in the serum concentration of insulin. At a concentration of 5×$10^{-10}$M, GLP-1 (7-37) was found to be capable of mediating an increase in serum insulin levels (32-fold). Even at a concentration of 5×$10^{-11}$M, GLP-1 (7-37) delivered a 15-fold increase in insulin levels whereas GLP-1 (1-37) was without effect.

This experiment shows that GLP-1 (7-37) is more than 1,000-fold more potent than GLP-1 (1-37) in stimulating insulin expression in vivo. In addition, the GLP-1 peptides had no effects on the release of the peptide hormones glucagon and somatostatin in these same experiments. Thus, the stimulatory effects of GLP-1 are specific for the beta cells and do not act on pancreatic alpha or delta cells.

TABLE 2

| | | Insulin Produced (picograms/ml) at Peptide Concentration | | | | |
|---|---|---|---|---|---|---|
| | Time (Minutes) | 5 × $10^{-7}$M | 5 × $10^{-8}$M | 5 × $10^{-10}$M | 5 × $10^{-11}$M | 5 × $10^{-12}$M |
| GLP-1 (7-37) | 0 | 50 | 925 | 205 | 160 | 50 |
| | 1 | 6600 | 20,700 | 7400 | 2400 | 50 |
| | 2 | 4700 | 10,500 | 1800 | 1700 | 50 |
| | 3 | 1700 | 4,000 | 760 | 1900 | 98 |
| GLP-1 (1-37) | 0 | 1400 | 3,000 | 500 | 340 | 50 |
| | 1 | 4700 | 6,000 | 600 | 180 | 50 |
| | 2 | 2900 | 2,000 | 640 | 230 | 160 |
| | 3 | 2200 | 2,000 | 430 | 340 | 50 |

Example 4

In order to determine whether glucagon-like proteins were capable of affecting cellular cAMP levels the effects of GLP-1 (7-37) and GLP-1 (1-37) on cAMP levels in RINS-38 insulinoma cells was determined (Expt I) and Expt II, respectively. Cells were grown as described in Example 1, in 26 well culture dishes. Varying amounts of glucogon-like peptides were added to culture wells in triplicate. After permitting incubation for 10 minutes the total cell media was examined for cAMP, and the concentration of cAMP was determined. The results of this experiment are shown in Table 3. 20 ul from each culture well was assayed.

TABLE 3

| Peptide Concentration (M) | pMOLES OF cAMP PRODUCED Expt I | Expt II |
|---|---|---|
| 0 | 140 | 91 |
| $10^{-6}$ | 400 | 170 |
| $10^{-7}$ | 370 | 120 |
| $10^{-8}$ | 494 | 160 |
| $10^{-9}$ | 515 | 100 |
| $10^{-10}$ | 253 | 90 |
| $10^{-11}$ | 533 | 90 |

This experiment reveals that GLP-1 (7-37) was capable of stimulating cAMP levels even when present at a concentration of $10^{-11}$M. The increase in cAMP levels is an indication that GLP-1 (7-37) is capable of interacting with cellular receptors.

Example 5

Figure 3:
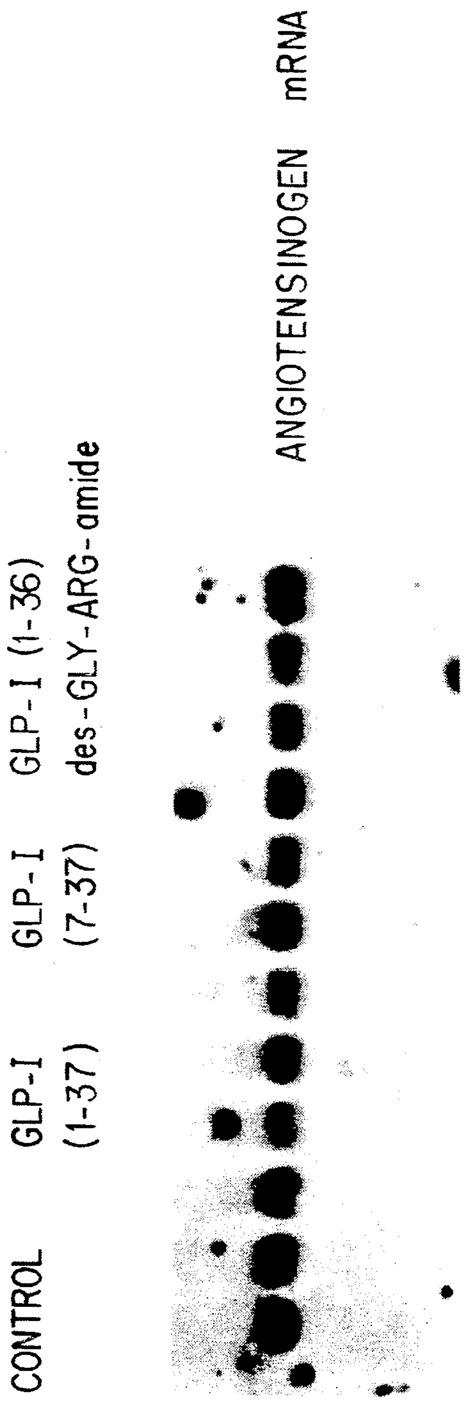
FIG. 3 shows the effects of GLP-1 peptides on angiotensingen mRNA levels in rat insulinoma cells.
Figure 4:
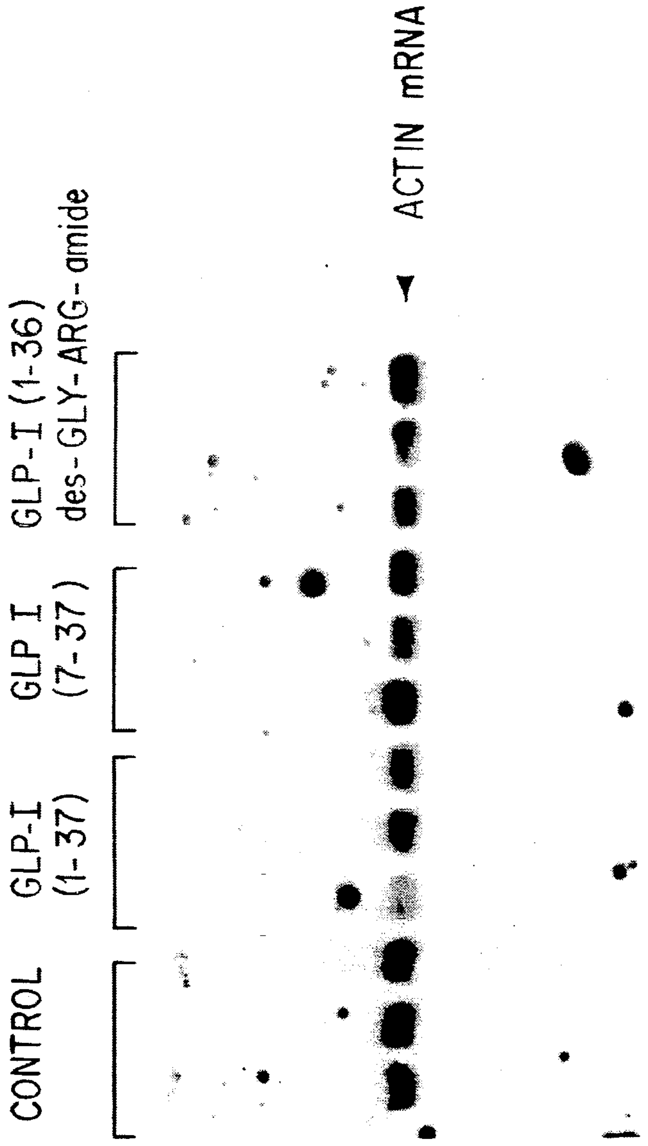
FIG. 4 shows the effects of GLP-1 peptides on acting mRNA levels in rat insulinoma cells.

In order to demonstrate that the effects of GLP-1 (1-37), GLP-1 (1-36) and GLP-1 (7-37) were specific for insulin, and were not capable of inducing or provoking non-specific gene expression, the effect of these peptides on the levels of actin and angiotensinogen mRNAs were conducted. RIN-38 insulinoma cells were grown as described in Example 1 and incubated in the presence of GLP-1 (1-37), GLP-1 (7-37), or GLP-1 (1-36) des-Gly arg (Peninsula Laboratories). In all cases the concentration of peptides was $10^{-7}$M. Incubations were for six hours. Messenger RNAs specific for insulin, actin, or angiotensinogen were identified by Northern hybridization as described in Example 1. The results of this experiment are shown in FIG. 2 (insulin mRNA); FIG. 3 (anginotensinogen mRNA); and FIG. 4 (actin mRNA). mRNA levels were determined in arbitrary densitometric units obtained from scanning films of the RNA gels of FIGS. 2, 3, and 4. The mRNA levels are shown in Table 4.

TABLE 4

EFFECTS OF GLUCAGON-LIKE PEPTIDES ON CELLULAR LEVELS OF mRNAs ENCODING INSULIN, ACTIN AND ANGIOTENSINOGEN IN RIN-38 INSULINOMA CELLS

| PEPTIDE* | MESSENGER RNAs INSULIN | ACTIN | ANGIOTENSINOGEN |
|---|---|---|---|
| GLP-I (7-37) | 4.23 ± 0.74 | 0.82 ± 0.08 | 2.78 ± 0.46 |
| GLP-I (1-37) | 1.87 ± 0.56 | 0.91 ± 0.02 | 2.25 ± 0.20 |
| GLP-I (1-36) des-Gly Arginine-amide | 2.78 ± 0.80 | 0.88 ± 0.03 | 2.56 ± 0.22 |
| Control (no peptide) | 1.28 ± 0.23 | 0.89 ± 0.05 | 2.67 ± 0.31 |

Example 6

Figure 5:
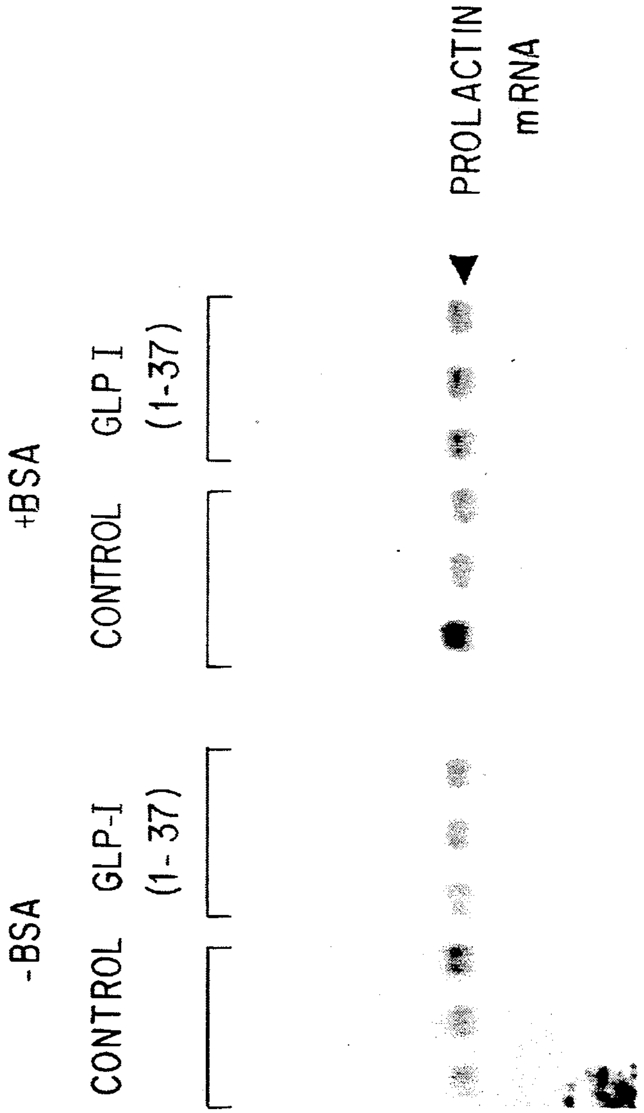
FIG. 5 shows the effect of GLP-1 (1-37) on prolactin mRNA levels in GH4 cells.
Figure 6:
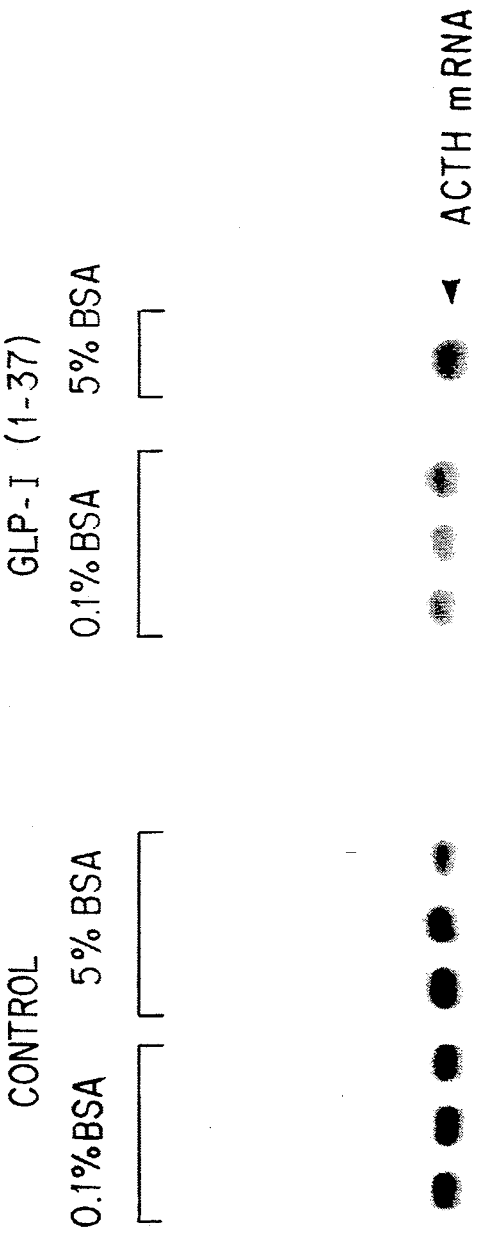
FIG. 6 shows the effects of GLP-1 (1-37) on ACTH mRNA levels in AtT-20 cells.

GLP-1 (1-37) was examined to determine whether it could induce the biosynthesis of hormones other than insulin. Thus, GLP-1 (1-37) (at a concentration of $10^{-7}$M) was added to a rat islet glucagon-producing cell line and two pituitary cell lines (GH4 and AtT-20) which were capable of producing the hormones prolactin and ACTH, respectively, and the amount of hormone specific mRNA produced was determined after 24 hours as described in Example 1. Prolactin mRNA levels in GH4 pituitary cells after incubation with GLP-1 peptides is shown in FIG. 5. ACTH mRNA levels in AtT-20 pituitary cells after incubation with GLP-1 peptides is shown in FIG. 6. These experiments revealed that GLP-1 (1-37) did not have any detectable effect upon the amount of mRNA which encodes these peptide hormones.

Example 7

The effect of GLP-1 (7-37) on the transcription of the insulin and actin genes in RIN-38 insulinoma cells was investigated. Gene transcription rates were determined by quantification of nascent glucagon and beta-actin RNA transcripts in nuclei from control and TPA treated cells. Nuclear RNA was hybridized to an excess of cloned specific DNA bound to nitrocellulose and the filters were washed as described by McKnight, G. S. et al, (*J. Biol. Chem.* 254:9050-9058 (1979)). Rat glucagon (Heinrich, G. et al, *Endocrinology,* 115: 1-6 (1984)) and, for control, chicken beta-actin cDNAs, provided by Dr. D. Cleveland, the Johns Hopkins University School of Medicine, Baltimore, Maryland, were used. Hybridization efficiency was controlled through the addition of the hybridization solution of [$^3$H] UTP glucagon cRNA. Experiments were done in duplicate and values are expressed in ppm/kb of cDNA insert, corrected for efficiency of hybridization (40-50%). Cells were incubated with GLP-1 (7-37) at a concentration of $10^{-7}$M for 4 hours. Nuclei were prepared from cells at 0, 1 and 4 hours and nascent insulin gene and actin gene transcripts were assessed by the nuclear run on assay (McKnight, G. S. et al *J. Biol. Chem.* 254;9050-9058 (1979). The experiment shows that GLP-1 (7-37) increases the rate of insulin gene transcription, but has no detectable effect upon the rate of actin gene expression.

TABLE 5

EFFECT OF GLUCAGON-LIKE PEPTIDE 1 (7-37) ON TRANSCRIPTION OF THE INSULIN AND ACTIN GENES IN RIN-38 INSULINOMA CELLS

| TIME (hrs) | INSULIN GENE | ACTIN GENE |
|---|---|---|
| 0 | 17.4 | 34.1 |
| 1 | 76.2 | 29.9 |
| 4 | 9.0 | 25.0 |

Having now fully described this invention, it will be apparent to one of ordinary skill in the art that the same may be carried out with minor modifications which do not effect the content or spirit thereof.

What is claimed is:

1. A molecule selected from the group consisting of:

(a) a peptide having the amino acid sequence:

His—Ala—Glu—Gly—Thr—Phe—Thr—Ser—Asp—

Val—Ser—Ser—Tyr—Leu—Glu—Gly—Gln—Ala—

Ala—Lys—Glu—Phe—Ile—Ala—Trp—Leu—Val—

Lys—Gly—Arg—Gly;

and (b) a derivative of said peptide (a), wherein said derivative is selected from the group consisting of:

(1) a pharmaceutically acceptable acid addition salt of said peptide;

(2) a pharmaceutically acceptable carboxylate salt of said peptide;

(3) a pharmaceutically acceptable lower alkyl ester of said peptide; and, (4) a pharmaceutically acceptable amide of said peptide wherein said pharmaceutically acceptable amide is selected from the group consisting of amide, lower alkyl amide and lower dialkyl amide;

wherein said molecule is substantially free of natural contaminants, and has an insulinotropic activity which exceeds the insulinotropic activity of GLP-1 (1-36) or GLP-1 (1-37).

2. The molecule of claim 1 which is said peptide (a).

3. The molecule of claim 1 which is said derivative (b) of said peptide (a).

4. The molecule of claim 3, wherein said amide is selected from the group consisting of a lower alkyl amide and a lower dialykyl amide.

5. An insulintropic composition which comprises an insulinotropic molecule in an amount effective to stimulate insulin secretion in a patient for treatment of maturity onset diabetes mellitus, said molecule being selected from the group consisting of:

(a) a peptide having the amino acid sequence:

His—Ala—Glu—Gly—Thr—Phe—Thr—Ser—Asp—

Val—Ser—Ser—Tyr—Leu—Glu—Gly—Gln—Ala—

Ala—Lys—Glu—Phe—Ile—Ala—Trp—Leu—Val—

Lys—Gly—Arg—Gly;

and (b) a derivative of said peptide (a), wherein said derivative is selected from the group consisting of:

(1) a pharmaceutically acceptable acid addition salt of said peptide;

(2) a pharmaceutically acceptable carboxylate salt of said peptide;

(3) a pharmaceutically acceptable lower alkyl ester of said peptide; and, (4) a pharmaceutically acceptable amide of said peptide wherein said pharmaceutically acceptable amide is selected from the group consisting of amide, lower alkyl amide and lower dialkyl amide;

wherein said molecule has an insulinotropic activity which exceeds the insulinotropic activity of GLP-1 (1-36) or GLP-1 (1-37); said molecule combined in admixture with a suitable pharmaceutically acceptable carrier.

6. The insulinotropic composition of claim 5, wherein said insulinotropic molecule is said peptide (a).

7. The insulinotropic composition of claim 5, wherein said insulinotropic molecule is said derivative (b) of said peptide (a).

8. A method for treating maturity onset diabetes mellitus in an individual in need of such treatment, wherein said method comprises providing an amount of an insulintropic molecule sufficient to treat said diabetes; wherein said molecule is selected from the group consisting of:

(a) a peptide having the amino acid sequence:

His—Ala—Glu—Gly—Thr—Phe—Thr—Ser—Asp—

Val—Ser—Ser—Tyr—Leu—Glu—Gly—Gln—Ala—

Ala—Lys—Glu—Phe—Ile—Ala—Trp—Leu—Val—

Lys—Gly—Arg—Gly;

and (b) a derivative of said peptide (a), wherein said derivative is selected from the group consisting of:

(1) a pharmaceutically acceptable acid addition salt of said peptide;

(2) a pharmaceutically acceptable carboxylate salt of said peptide;

(3) a pharmaceutically acceptable lower alkyl ester of said peptide; and, (4) a pharmaceutically acceptable amide of said peptide wherein said pharmaceutically acceptable amide is selected from the group consisting of amide, lower alkyl amide and lower dialkyl amide;

wherein said molecule has an insulinotropic activity which exceeds the insulinotropic activity of GLP-1 (1-36) or GLP-1 (1-37).

9. The method for treating maturity onset diabetes mellitus of claim 8, wherein said insulinotropic molecule is said peptide (a).

10. The method for treating maturity onset diabetes mellitus of claim 8, wherein said insulinotropic molecule is said derivative (b) of said peptide (a).

* * * * *

UNITED STATES PATENT AND TRADEMARK OFFICE

CERTIFICATE OF CORRECTION

PATENT NO. : 5,120,712

DATED : June 9, 1992

INVENTOR(S) : HABENER

It is certified that error appears in the above-indentified patent and that said Letters Patent is hereby corrected as shown below:

column 2, line 18, delete "*Parsons*" and insert therein --Parsons--; column 2, line 18, delete "Parle" and insert therein --Park--; column 2, line 21, delete "(1976)" and insert therein --(1979)--.

In the Drawings, delete Fig. 1A and 1B:

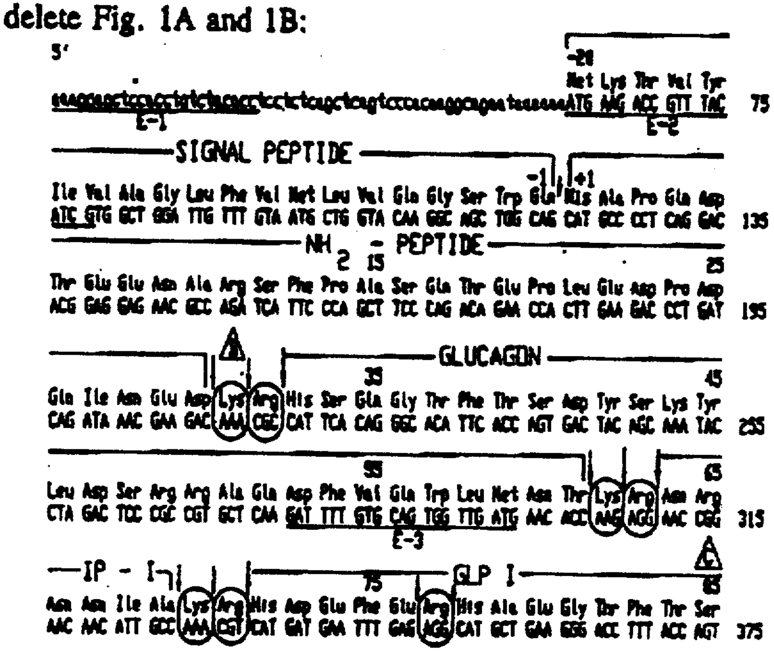

FIG.1A

UNITED STATES PATENT AND TRADEMARK OFFICE

CERTIFICATE OF CORRECTION

PATENT NO. : 5,120,712

DATED : June 9, 1992

INVENTOR(S) : HABENER

It is certified that error appears in the above-indentified patent and that said Letters Patent is hereby corrected as shown below:

FIG.1B

CERTIFICATE OF CORRECTION

PATENT NO. : 5,120,712

DATED : June 9, 1992

INVENTOR(S) : HABENER

It is certified that error appears in the above-indentified patent and that said Letters Patent is hereby corrected as shown below:

And replace therein corrected Figure 1A and 1B:

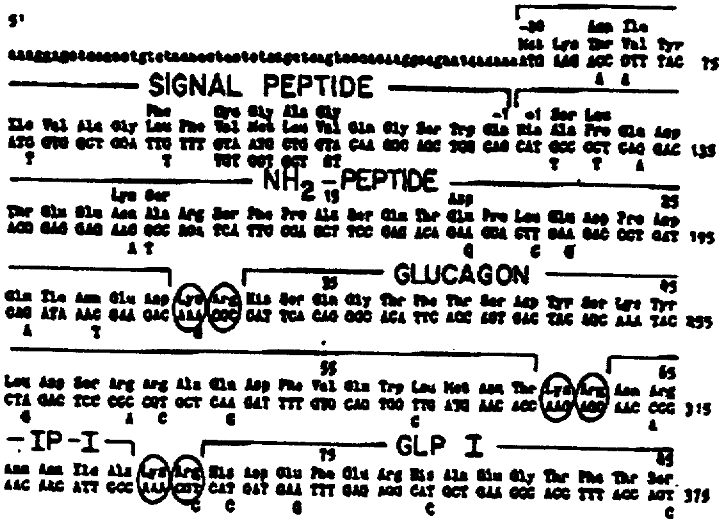

UNITED STATES PATENT AND TRADEMARK OFFICE
CERTIFICATE OF CORRECTION

PATENT NO. : 5,120,712

DATED : June 9, 1992

INVENTOR(S) : HABENER

It is certified that error appears in the above-indentified patent and that said Letters Patent is hereby corrected as shown below:

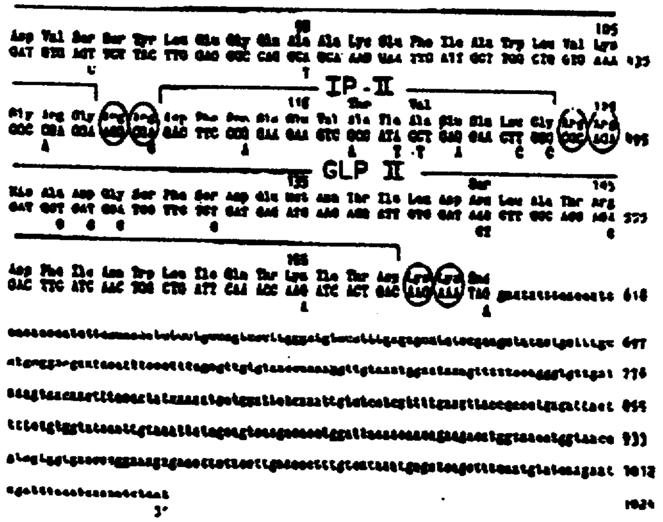

UNITED STATES PATENT AND TRADEMARK OFFICE

CERTIFICATE OF CORRECTION

PATENT NO. : 5,120,712

DATED : June 9, 1992

INVENTOR(S) : HABENER

It is certified that error appears in the above-indentified patent and that said Letters Patent is hereby corrected as shown below:

Column 2, line 4, delete "*(Nature)*" and insert therein --*Nature*--; line 9, delete "poteolytically" and insert therein --proteolytically--; line 15, before "dipeptides" insert --arginine --; line 17, delete "discreet" and insert therein --discrete--; line 5, delete the comma "," between "beta" and "cells"

Column 3, lines 21-22, delete "angiotensingen" and insert therein --angiotensinogen--; line 23, delete "acting" and insert therein --actin--; line 38, delete "G.R." and insert therein --G.I.--

Column 4, line 20, between "OH" and "OM", insert a comma --,--; line 22, delete "(C1-C6)" and insert therein --($C_1$-$C_6$)--; line 22, delete "R2" and insert therein --$R^2$--; line 23, delete "R3" and insert therein --$R^3$--; line 26, delete "$H_2$N-X-CD" and insert therein --$H_2$N-X-CO--.

Column 7, line 2, before "respectively" insert --and poly(methylmethacrylate) microcapsules,--; line 63, delete "(1-37" and insert therein --(1-37)--.

UNITED STATES PATENT AND TRADEMARK OFFICE

CERTIFICATE OF CORRECTION

PATENT NO. : 5,120,712 Page 6 of 6

DATED : June 9, 1992

INVENTOR(S) : HABENER

It is certified that error appears in the above-indentified patent and that said Letters Patent is hereby corrected as shown below:

Column 8, line 16, delete "$5X10^{10}M$" and insert therein --$5X10^{-10}M$--; line 16, delete "$5X10^{12}M$" and insert therein --$5X10^{-12}M$--; line 67, delete "(Expt I) and Expt II, respectively" and insert therein --(Expt I and Expt II, respectively)--.

Column 9, line 1, delete "glucogon" and insert therein --glucagon--.

Column 10, line 33, after "(1979)." insert --The results of this experiment are shown in Table 5.--.

Column 11, claim 5, line 1, delete "insulintropic" and insert therein --insulinotropic--.

Column 12, claim 8, line 4, delete "insulintropic" and insert therein --insulinotropic--.

Signed and Sealed this

Twelfth Day of August, 1997

Attest:

Bruce Lehman

BRUCE LEHMAN

*Attesting Officer* *Commissioner of Patents and Trademarks*

UNITED STATES PATENT AND TRADEMARK OFFICE
Certificate

Patent No. 5,120,712 Patented: June 9, 1992

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Joel Habener, Newton Highlands, MA; and Svetlana Mojsov, New York, NY.

Signed and Sealed this Sixteenth Day of November 2004.

CHRISTINA CHAN
*Supervisory Patent Examiner*
Art Unit 1644